United States Patent
Sabin et al.

[19]

[11] Patent Number: 6,010,523

[45] Date of Patent: Jan. 4, 2000

[54] FORCEPS INSTRUMENT, ESPECIALLY OF THE BIOPSY FORCEPS TYPE

[75] Inventors: Pierre Jean-Claude Sabin, 696 rue Robert Pinchon, 76230 Bois Guillaume; Jean Louis Sabin, 159 Les Moubins, 97220 Sainte Luce; Jean-Marie Hugueny, Vernus, 69430 Regnie-Durette, all of France

[73] Assignees: Pierre Jean-Claude Sabin, Bois Guillaume; Jean Louis Sabin, Sainte Luce; Jean-Marie Hugueny, Regnie-Durette; Antoine Warnier, Paris, all of France

[21] Appl. No.: 08/896,532

[22] Filed: Jul. 18, 1997

[30] Foreign Application Priority Data

Jul. 18, 1996 [FR] France .................................. 96 09023

[51] Int. Cl.$^7$ .................................................. A61B 17/28
[52] U.S. Cl. .......................... 606/205; 606/205; 606/206; 606/207; 606/208; 600/562; 600/563; 600/564; 600/565
[58] Field of Search ...................... 606/205, 206, 606/207, 208; 600/562, 563, 564, 565

[56] References Cited

U.S. PATENT DOCUMENTS

| | | |
|---|---|---|
| 3,895,636 | 7/1975 | Schmidt . |
| 5,275,615 | 1/1994 | Rose . |
| 5,290,309 | 3/1994 | Kothe . |
| 5,425,743 | 6/1995 | Nicholas .................................. 606/208 |
| 5,478,350 | 12/1995 | Kratsch et al. .......................... 606/205 |

FOREIGN PATENT DOCUMENTS

| | | |
|---|---|---|
| 0 380 874 | 8/1990 | European Pat. Off. . |
| 0 573 817 | 12/1993 | European Pat. Off. . |
| WO 95/07662 | 3/1995 | WIPO . |

*Primary Examiner*—Michael Buiz
*Assistant Examiner*—Vy Quang Bui
*Attorney, Agent, or Firm*—Young & Thompson

[57] ABSTRACT

The invention relates to a biopsy forceps having two jaw-pieces (9) capable of being moved away from and of being moved towards each other while a maneuvering element (2) is sliding in a sheath (3). The two jaw-pieces (9) are pivoted about a ball (20) fixed on the end of the maneuvering element. The jaw-pieces (9) are partly housed in a passage in the end of the sheath (3). They are guided by a rod (8) while they are being moved away from each other and by the end surface of the passage in the sheath (3) while they are being moved towards each other.

13 Claims, 2 Drawing Sheets

FORCEPS INSTRUMENT, ESPECIALLY OF THE BIOPSY FORCEPS TYPE

The present invention relates to a forceps instrument, such as, especially, a biopsy forceps, that is to say a forceps having two jaw-pieces capable of being moved away from each other, of being moved closer to each other and, while they are moving closer to each other, of cutting or detaching a specimen of body tissue which is seized between the two jaw-pieces of the forceps and which can subsequently be recovered outside the body.

However, the invention also extends to other instruments which can be used in medicine or in surgery, such as, for example, forceps instruments having no cutting effect, for example for providing a clamping effect, or retractors, or else scissors for chemical use, or any other instrument of this kind having two elements, one of which at least is capable of being moved away from and moved closer towards the other.

Typically, the currently known biopsy forceps have two jaw-pieces capable of being moved away from each other or moved closer to each other, these being pivoted on the end of an elongate, rigid or flexible, sheath or tube, inside which a cable can slide, this cable being provided at its other end with means for it to be manoeuvred by the operator. These instruments have pivoted links designed to amplify movement between the control means formed by the cable and the jaw-pieces proper.

These forceps are mechanically complex and consist of about ten components at least. They are therefore expensive, difficult to fit and subject to wear and to failures. At the linkage to the cable, they lead to torsional effects inducing fatigue in the cable which may cause it to break. Other components, too, may be exposed to excessive stresses, so that in the final analysis these forceps have a large number of drawbacks.

The present invention aims to remedy these drawbacks and to provide a forceps instrument, especially a biopsy forceps, of extremely simple design, having a very limited number of components, eliminating any excessive force capable of leading to wear of the components or to twisting of the maoeuvring cable, and enabling complex movements to be made, if required, in a simple manner, while maintaining very great precision in the movements of the jaw-pieces.

The subject of the invention is a forceps instrument, in particular of the biopsy-forceps type, comprising, on the end of a rigid or flexible sheath, in which may slide an elongate manoeuvring element, preferably a cable, two jaw-pieces, one of which, at least, is capable of being moved away from and of being moved towards the other when the said manoeuvring element slides axially in the end of the sheath, characterized in that the said jaw-piece or jaw-pieces, capable of being moved away from and of being moved towards each other have, in the extension of a part of the jaw-pieces acting as the jaws proper, an arm, which goes progressively towards the axis of the sheath so as to form a first, internal, inclined surface, going progressively towards the axis and facing the latter, a second, external, inclined surface also going progressively towards the axis and facing the internal surface of the end of the sheath, the said arm having a convex excrescence capable of sliding substantially against the said internal surface of the end of the sheath, the said excrescence having, facing the axis, a substantially spherical concave hollow cavity, in that the said sheath has, near its end beyond which the said jaw proper extends, a transverse element, such as a rod against which the said internal surface of the said arm slides, and in that the said elongate manoeuvring element terminates in a ball housed in the said spherical cavity so that, when the said elongate manoeuvring element or cable is moved towards the free end of the sheath, it pushes the said jaw-piece back beyond the end, thus causing the internal surface of the said arm, which slides over the said transverse element, to pivot by a ramp effect, moving the jaw of the jaw-piece away from the other jaw, the said movement away from the other jaw being allowed by the inclination of the said external surface which protrudes from the end of the internal surface of the sheath, the said excrescence of the arm pivoting, during this movement, about the said ball while still being guided in the said sheath, the reverse movement of the manoeuvring element causing the jaw-pieces to come together by a reverse movement.

Preferably, the end of the sheath, especially when the sheathe is flexible, is formed by a rigid element fixed to one end of the sheath proper by one end of the rigid element, the other, free end of which supports the transverse element or rod, preferably in two crenel-shaped extensions so that the geometrical axis of the rod is located near the bottoms of the crenels.

Preferably, the said internal surface of the end of the sheath, or of its rigid end element, is plane, the internal and external surfaces of the arm or arms then being plane surfaces or geometrically cylindrical surfaces with a generatrix parallel to the said internal surface of the end of the sheath and to the rod, and the external surface of the excrescence of the arm also being cylindrical.

Advantageously, the cross-section of the end of the sheath, or of its rigid end element, delimits internally a rectangle, in particular a square, the said internal surface of the end of the sheath, or of its rigid end element, being generated by one side of the rectangle.

Thus, by virtue of the invention, the internal surface of the jaw-piece arm may have a straight profile, or on the contrary, a profile which may vary, going progressively towards the axis of the sheath as it penetrates further into the sheath, thereby enabling the kinematics of the movement of the jaw-pieces away from each other to correspond to the shape of the ramp thus formed. The external face of the said arm is then shaped also when being moved closer to the axis, preferably so as to constantly slide on the end of the internal surface of the sheath and thus to avoid any free movement of the arm between the said rod and the internal surface of the sheath.

Beyond the arm, the jaw-piece has the part forming the jaw proper, which may be of any shape suited to the desired use thereof.

The jaw of the jaw-piece may, for example, be produced in the form of a spoon having a cutting perimeter in the case of a biopsy forceps.

As a variant, the shape of the jaw may be that of a flat jaw-piece, for example in order to produce a gripping or clamping effect.

As another variant, the jaw may be in the form of a scissors cutting blade in order to produce a cutting instrument.

In general, the two jaw-pieces are symmetrical and undergo perfectly symmetrical movements with respect to a plane passing through the axis of the end of the sheath and the axis of the rod.

However, in a variant, one of the jaw-pieces may be produced so as to remain rotationally stationary and to undergo only a sliding movement while the other undergoes a sliding and pivoting movement with respect to the sheath.

During use, it may be desired for the jaw-piece, when moving away, also to move axially with respect to the element to be treated, for example, an organ. In this case, the sheath will remain stationary with respect to the organ to be treated and the manoeuvring means, such as the cable, will undergo a translational movement in the sheath.

On the other hand, it may be desired for the jaw-pieces to undergo only a movement away from or towards the object or organ to be treated and in this case, it is the manoeuvring element which will remain stationary while the sheath will be moved translationally along this elongate manoeuvring element.

For this purpose, the manoeuvring element and the sheath include means which are designed to act, in turn, as means of holding one of the manoeuvring element and the sheath in position with respect to the organ to be treated and as means of moving the other of these, respectively.

It will be understood that a forceps instrument has thus been produced which is mechanically very simple and which is composed of a very small number of components, namely the two jaw-pieces, the transverse rod, the ball which terminates the sheath, and optionally a tubular section added onto the end of the sheath and forming the internal surface for guiding and receiving, on its end, the rod.

The resulting instrument is easy to assemble and dismantle, simple to maintain and almost free of the risk of breaking or of failing, the more so because the manoeuvring element, such as a cable, is exposed to no torsional stress, its angular position about the axis of the sheath being entirely free, by the ball sliding inside the concave cavity of the jaw-piece arms.

Other advantages and characteristics of the invention will appear on reading the following description, given by way of non-limiting example, and with reference to the appended drawing in which.

Figure 1:
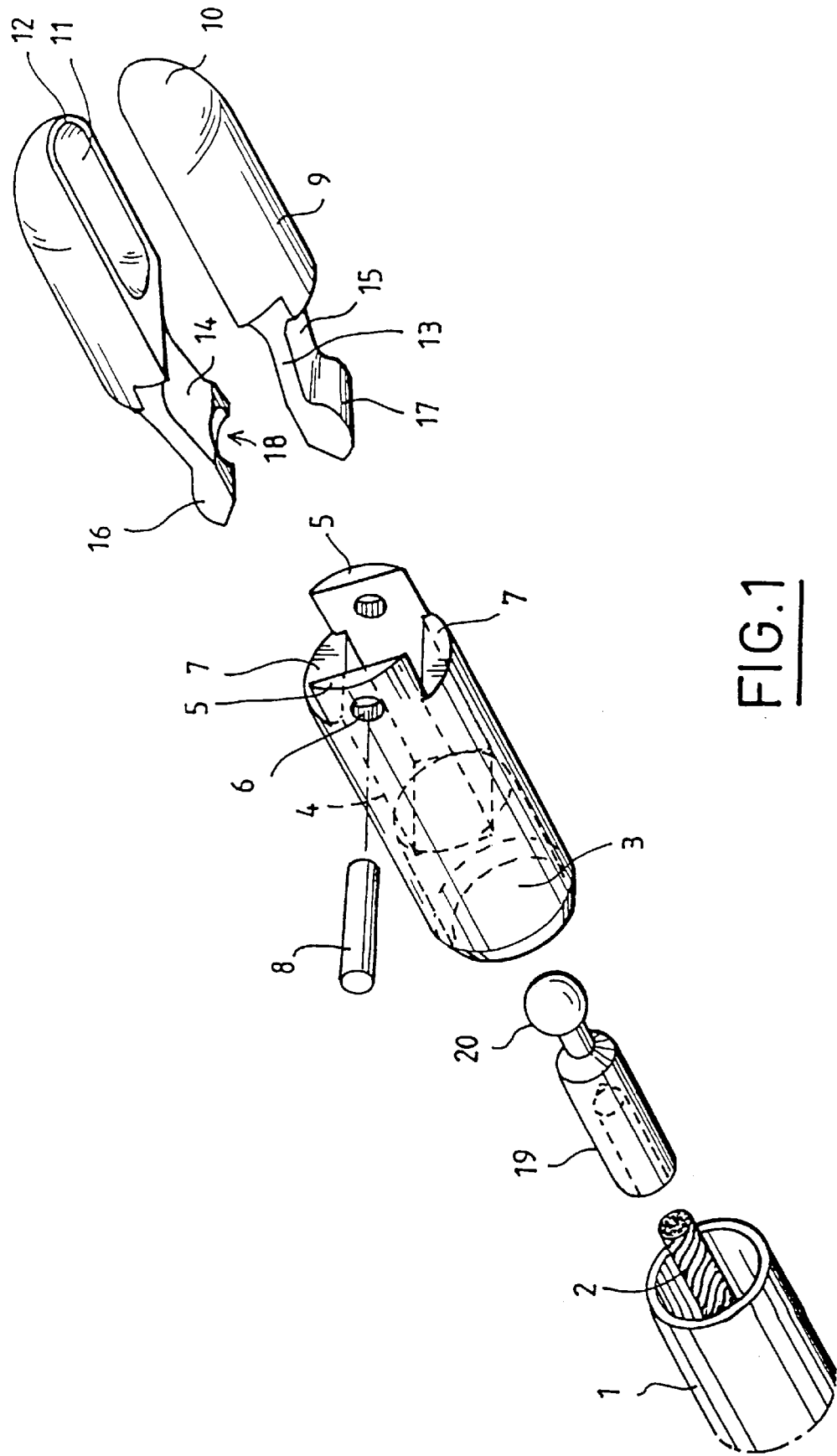
FIG. 1 shows an exploded perspective view of the instrument according to the invention.

The biopsy forceps shown in the figures has an elongate sheath 1 inside which a semi-rigid cable 2 may move longitudinally, one of the ends, not shown, of which cable is connected to a manoeuvring grip of the usual type in this kind of forceps. Advantageously, means are provided for holding either the sheath or the cable in position with respect to the organ to be treated and for moving that one, of the sheath and the cable, which is not held in position.

The sheath 1 has, on its end, a metal tubular element 3, the outer surface of which is cylindrical and which includes a central passage 4 of rectangular or square cross-section. At its end remote from the sheath, the cylindrical component 3 is cut into the form of crenels so as to form two extensions 5 through which pass aligned holes 6, the common geometrical axis of which is located slightly above the plane of the two lowermost edges 7 of the crenels. Thus, the bottom part of the holes 6 lies substantially in the plane of these lowermost edges. A cylindrical rod 8 is forced into the holes 6, the rod thus extending transversely to the upper end of the square cross-sectional passage 4.

The forceps has two identical jaw-pieces 9, those parts of which jaw-pieces which form the actual jaws 10 extend beyond the crenellate end of the tubular component 3 and have, in the usual manner, cavities 11 whose edges form a peripheral cutting lip 12. The jaw-pieces 9 are each extended inside the component 3, by an arm 13 which passes between the rod 8 and the plane internal surface of the passage 4 facing the rod. The arm 13 has an internal surface 14 which is generated by a generatrix perpendicular to the plane of FIG. 2 and which, starting from the rod 8, goes progressively towards the axis of the instrument until meeting this axis almost tangentially. Beyond the rod, in the position shown in FIG. 2, the surface 14 again curves in the direction of the axis, this time towards the top end, so as substantially to surround the rod, as may be clearly seen in FIG. 2.

Figure 2:
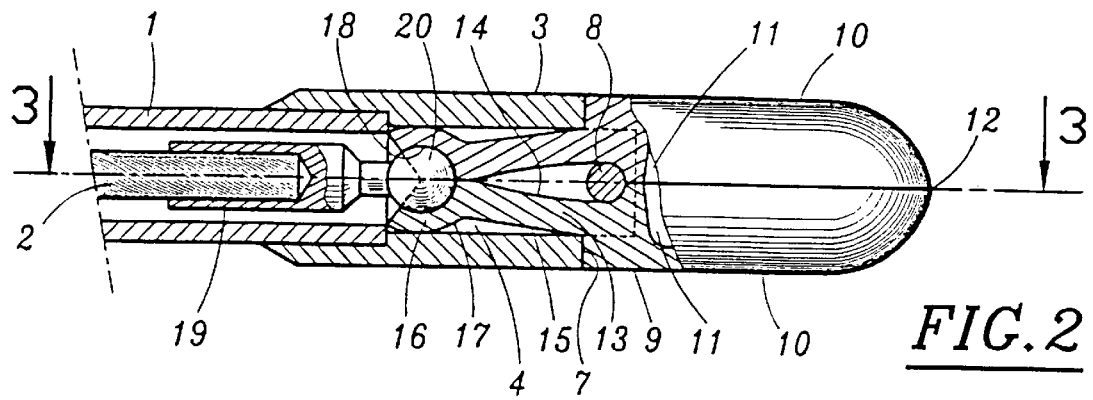
FIG. 2 shows an axially sectional view in a plane perpendicular to the rod, of the instrument.

The arms 13 also have an outer surface 15 which also tends to move towards the axis on going downwards and which is such that the thickness of the arm 13, in the direction perpendicular to the axis axis, lying in the plane of FIG. 2, tends to decrease progressively, this thickness being almost equal to the distance between the rod 8 and the plane internal wall of the component 3 at the edge 7. The arm 13 has a convex end excrescence 16, the external surface 17 of which has approximately the shape of a cylinder having a circular base, the diameter of which is slightly less than the distance separating the two plane internal surfaces, facing each other, of the component 3. The excrescence 16 has, on the inside, a cavity 18 of spherical shape.

The end of the cable 2 carries an end-fitting 19 crimped onto the cable and having, at its free end, a spherical tip or ball 20 which is housed in the joint formed by the two spherical cavities 18 of the two jaw-pieces 9.

In order to assemble the instrument, the two jaw-pieces 9 are suitably placed on the ball 20, then they are inserted into the component 3 and, finally, the rod 8 is fitted.

Figure 3:
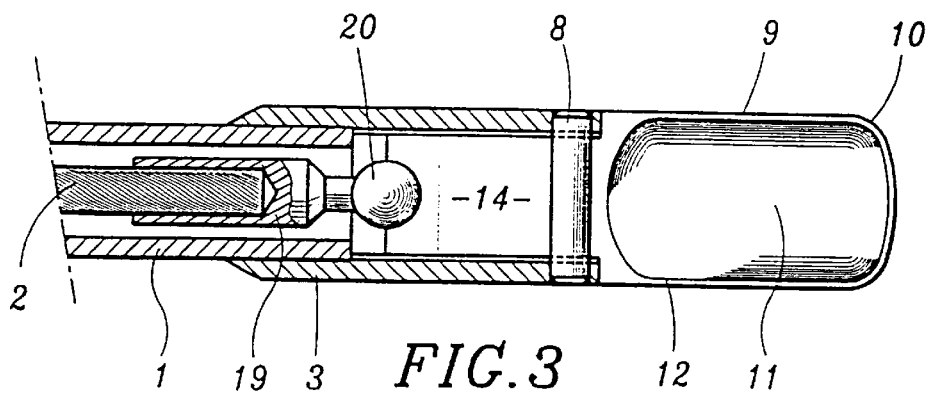
FIG. 3 shows an axial sectional view of the instrument in an axial plane of the rod.
Figure 4:
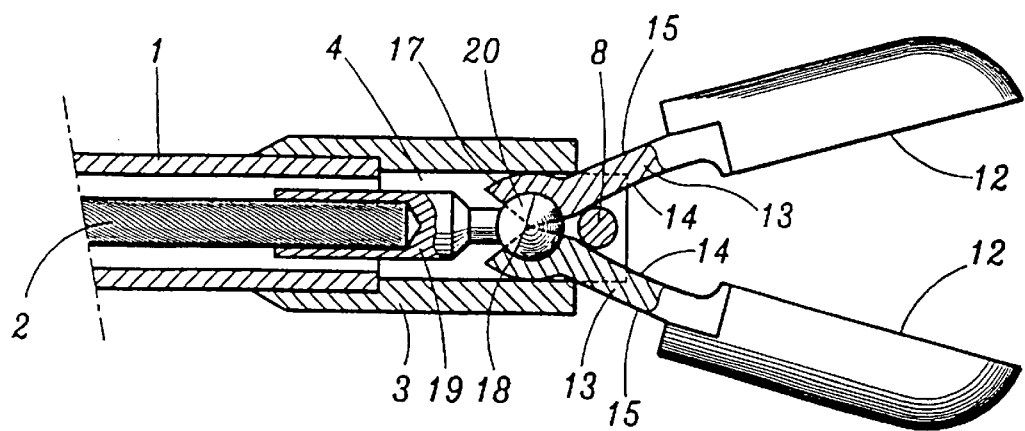
FIG. 4 shows a view similar to FIG. 2 in a position in which the jaw-pieces are apart.

When, starting from the closed forceps position shown in FIGS. 2 and 3, the cable is pushed upwards, in the direction of the arrow, the ball 20 pushes the two jaw-pieces upwards so that the surfaces 14, which slide on the rod 8, rapidly produce a ramp effect which tends to move the two arms 13 apart, causing them to pivot about the ball 20, while still keeping the two excrescences 16 going around the ball so that these ends remain guided in the square passage 4.

This rocking movement of the arms is progressively allowed because of the inclination of the external surface 15 of the arms, which avoids jamming and guides the arms as they rise above the rims 7. At the end of travel, the movement is stopped by the presence of the rod and the two jaw-pieces are in the position of maximum opening.

The jaw-pieces are closed by manoeuvring the cable 2 in the opposite direction to that of the arrow.

It will be understood that a biopsy forceps has thus been produced which is composed of a very small number of elements and whose mechanical simplicity makes it possible to eliminate virtually any risk of failure. Furthermore, the mechanical forces on such a forceps, which may be highly miniaturized, are perfectly distributed. Finally, rotating the cable 2 causes no jamming effect since the ball 20 can rotate freely in its spherical seat formed by the junction of the two cavities 18.

In addition, the biopsy-forceps tip described here is short in the axial direction thanks to the simplicity of its construction. Thus, it can move in guide tubes having small radii of curvature without any risk of jamming.

As a variant, the forceps tip may have asymmetrical jaw-pieces, one of which carries, for example, a single tooth and the other of which carries two teeth delimiting a space for receiving the single tooth of the complementary jaw-piece in the closed position of the forceps.

We claim:

1. Forceps instrument of the biopsy-forceps type, comprising, on the end of a rigid or flexible sheath (1,3), in which may slide an elongate maneuvering element (2), two jaw-pieces (9), one of which, at least, is capable of being moved away from and of being moved towards the other when said maneuvering element (2) slides axially in the end of the sheath (1,3), wherein said jaw-piece or jaw-pieces (9), capable of being moved away from and of being moved towards each other have, in the extension of a part of the jaw-pieces acting as the jaws proper (10), an arm (13), which goes progressively toward an axis (A—A) of the sheath (1,3) so as to form a first, internal, inclined surface (14), going progressively towards the axis (A—A) and facing the latter, a second, external, inclined surface (15) also going progressively towards the axis (A—A) and facing the internal surface of the end of the sheath (1,3), said arm (13) having a convex excrescence (16) capable of sliding substantially against said internal surface of the end of the sheath (1,3), said excrescence (16) having, facing the axis (A—A), a substantially spherical concave hollow cavity (18), wherein said sheath (1,3) has, near its end beyond which the said jaw proper (10) extends, a transverse element (8) against which the said internal surface (14) of the said arm (13) slides, and wherein said elongate maneuvering element (2) terminates in a ball (20) housed in said spherical cavity (18) so that, when said elongate maneuvering element (2) is moved towards the free end of the sheath (1,3), it pushes said jaw-piece (9) back beyond the end, thus causing the internal surface (14) of said arm (13), which slides over said transverse element (8), to pivot by a ramp effect, moving the jaw of the jaw-piece away from the other jaw, said movement away from the other jaw being allowed by the inclination of said external surface (15) which protrudes from the end of the internal surface of the sheath (1,3), said excrescence (16) of the arm pivoting, during this movement, about said ball (20) while still being guided in said sheath (1,3), the reverse movement of the maneuvering element (2) causing the jaw-pieces (9) to come together by a reverse movement.

2. Instrument according to claim 1, wherein the sheath (1,3) comprises a rigid element (3) fixed to one end of the sheath (1) proper by one end of the rigid element (3), the other, free end of which supports the transverse element (8).

3. Instrument according to claim 2, wherein the transverse element (8) is supported by two crenel-shaped extensions (5) so that a geometrical axis of the transverse element (8) is located near a bottom (7) of the crenels.

4. Instrument, according to claim 1, wherein said internal surface of the end of the sheath is planar, the internal (14) and external (15) surfaces of the arm or arms (13) then being planar surfaces or geometrically cylindrical surfaces with a generatrix parallel to said internal surface of the end of the sheath and to the transverse element (8), and the external surface (17) of the excrescence (16) of the arm also being cylindrical.

5. Instrument according to claim 4, wherein a cross-section of the end of the sheath delimits internally a rectangle, said internal surface of the end of the sheath being generated by one side of the rectangle.

6. Instrument according to claim 1, wherein said jaws have cavities (11) whose edges form a peripheral cutting lip (12).

7. Instrument according to claim 1, comprising two identical said jaw-pieces (9).

8. Instrument according to claim 1, comprising two asymmetric said jaw-pieces.

9. A forceps instrument for performing a biopsy, comprising:

a sheath with a rectangular cross-section space in one end thereof;

co-acting jaws with first ends slideably mounted in said rectangular space, said first ends of said co-acting jaws having interiors which together form a substantially spherical cavity; and an elongate maneuvering element having one end slideably carried inside said sheath, said one end having a ball thereon that is carried within said spherical cavity, wherein said co-acting jaws open and close with relative motion between said sheath and said maneuvering element that causes sliding motion of the co-acting jaws by means of said ball and spherical cavity connection.

10. The forceps instrument of claim 9, wherein each of said co-acting jaws comprises an arm joining said first end to an opposite operational end, said arm having an exterior surface that is spaced farther from an interior of said rectangular space at said first end than at said opposite end, when said co-acting jaws are closed.

11. The forceps instrument of claim 9, further comprising a connector joining said ball to said maneuvering element, said connector having an external diameter smaller than that of said ball, and wherein said spherical cavity has an opening at one side for said connector which has a smallest diameter smaller than that of said ball and larger than that of said connector.

12. The forceps instrument of claim 11, wherein said opening has frusto conical sides.

13. The forceps instrument of claim 9, wherein exteriors of said first ends together form a substantially external spherical surface which permits pivoting of said first ends about said ball with relative motion of said maneuvering element and said sheath.

* * * * *